United States Patent [19]

Willis

[11] 4,256,097

[45] Mar. 17, 1981

[54] ORTHOPEDIC APPARATUS FOR PROTECTING AND SUPPORTING A BONE JOINT

[76] Inventor: Robert E. Willis, 2020 Lippencott Dr., Flint, Mich. 48503

[21] Appl. No.: 361

[22] Filed: Dec. 29, 1978

[51] Int. Cl.³ .............................................. A61F 5/00
[52] U.S. Cl. ................................ 128/80 C; 128/80 F
[58] Field of Search ................ 128/80 R, 80 C, 80 F, 128/88; 3/22, 24, 26, 27; 2/22, 24

[56] References Cited

U.S. PATENT DOCUMENTS

| | | | |
|---|---|---|---|
| 2,467,907 | 4/1949 | Peckham | 128/80 C |
| 2,536,454 | 1/1951 | McIntyre | 128/80 F |
| 2,573,866 | 11/1951 | Murphy | 128/80 F |
| 2,827,897 | 3/1958 | Pawlowski | 128/80 F |
| 2,959,168 | 11/1960 | Shouk | 128/80 C |
| 3,055,359 | 9/1962 | Palmer | 128/80 C |
| 3,350,719 | 11/1967 | McClure, Jr. | 128/80 C |
| 3,533,106 | 10/1970 | Kremp | 2/22 |
| 3,581,741 | 11/1971 | Rosman | 128/80 C |
| 3,786,804 | 1/1974 | Lewis | 2/24 |
| 3,799,158 | 3/1974 | Gardner | 128/80 C |
| 3,826,251 | 7/1974 | Ross | 128/80 F |
| 3,955,565 | 5/1976 | Johnson | 128/89 R |
| 3,990,440 | 11/1976 | Gaylord, Jr. | 2/24 |

FOREIGN PATENT DOCUMENTS

| | | | |
|---|---|---|---|
| 79821 | 1/1920 | Austria | 128/80 C |
| 228221 | 11/1910 | Fed. Rep. of Germany | 128/88 |
| 20530 | 5/1918 | France | 128/94 |
| 508227 | 10/1920 | France | 128/88 |
| 1125183 | 10/1956 | France | 128/80 F |
| 1236669 | 6/1960 | France | 128/80 F |
| 2305166 | 10/1976 | France | 128/80 F |
| 1534434 | 12/1978 | United Kingdom | 128/80 C |

Primary Examiner—Robert W. Michell
Assistant Examiner—Arthur S. Rose
Attorney, Agent, or Firm—Wilson, Fraser, Barker & Clemens

[57] ABSTRACT

An orthopedic apparatus to be worn by a person such as an athlete, trauma victim or surgical patient, to protect and supplement the function of a bone joint. The apparatus comprises a first support member adapted to be placed on one lateral aspect of an appendage above the bone joint to be treated. A first rigid arm extends from the first support member and terminates in a male member adjacent the bone joint. A second support member is placed on the same lateral aspect of the appendage as the first support member and positioned below the bone joint to be treated. A second rigid arm extends upwardly from the second support member and terminates in a female member at a point adjacent the bone joint to be treated, such that the male and female members cooperate to form a ball and socket joint. The support members are secured to the appendage so that the ball and socket joint remains adjacent the bone joint to protect and supplement the function of the bone joint. Where needed, one appliance can be placed on each aspect, medial and lateral, of the appendage to be treated to provide added support and protection for the bone joint.

13 Claims, 11 Drawing Figures

ORTHOPEDIC APPARATUS FOR PROTECTING AND SUPPORTING A BONE JOINT

BACKGROUND OF THE INVENTION

1. Field of the Invention

The present invention relates generally to bone joint protectors and braces, and more particularly to a unique device which allows rotary movement of the bone joint while the apparatus is in place, supporting and protecting the bone joint. In many situations such as, for example, athletic injury recovery, surgical treatment recovery, and recovery from accident trauma, there is a need for an orthopedic apparatus which will provide some support to the bone joint and surrounding tissue while allowing mobility of the bone joint. Presently there is a need for a bone joint support and protecting apparatus which will allow movement of the bone joint in more than a single plane of motion during the recovery period.

2. Description of the Prior Art

The typical bone joint brace or support is constructed in such a fashion that it supports the bone joint adequately but allows movement of the affected appendage in only one plane. As is common knowledge in the medical arts, many bone joints employ a rotary motion in their normal operation such as, for example, the elbow, ankle, knee, wrist joint, etc.

One such prior art structure was designed to function as a knee brace. The brace included a brace joint formed by a forkhead structure and a flat-sided head held together by a pin. Two arms extended from the joint with one arm extending up the leg to a tie down structure and the second arm extending down the leg to a second tie down structure. The tie down structures held the brace joint adjacent the affected bone joint, while the appliance was in service.

In another prior art structure for a knee brace, a hinge was used which included a rivet having a head and a shank portion. The rivet head overlapped a washer which overlapped the upper end of a connecting bar. The rivet shank extended through a cylindrical hole in the washer, through a hole in the connecting bar, through a hole in a leg structure and terminated in an enlarged shank head. The diameter of the holes were substantially larger than the diameter of the shank below the enlarged head, such that the leg and connecting bar could slide relative to one another and rotate about the rivet. The shank was long enough to enable the leg structure to rock with respect to the connecting bar, thus, the hinge was able to supply substantial mobility to an injured knee.

SUMMARY OF THE INVENTION

The present invention concerns an orthopedic apparatus which is used to support and protect an injured bone joint. The apparatus includes a first support member which is secured to the affected appendage at a point above the bone joint. A first rigid arm extends downwardly from the first support member, and terminates in a male portion, which is generally a spherically shaped enlarged head or ball. A second support member is secured to the affected appendage below the bone joint. A second rigid arm extends upwardly toward the bone joint and terminates in a cup-shaped female member or socket. The female member or socket is configured to accept and retain the male member or spherically shaped ball as a ball and socket joint which allows substantial rotary motion of the affected bone joint.

It is an object of the present invention to provide an orthopedic apparatus capable of supplying support and protection to a bone joint which has been adversely affected by accident trauma, surgical repair or athletic injury.

It is another object of the present invention to provide an orthopedic apparatus which will assist in the rotary motion of the affected bone joint, while providing support and protection for the bone joint.

A further object of the present invention is to provide an orthopedic apparatus which may be fabricated from a minimum of independent parts to reduce the cost of producing such apparatus.

It is another object of the present invention to supplement the flexion and extension of a ball joint and, at the same time, provide maximum protection against new injury as well as against aggravation of an old injury.

DESCRIPTION OF THE PREFERRED EMBODIMENTS

Figure 1:
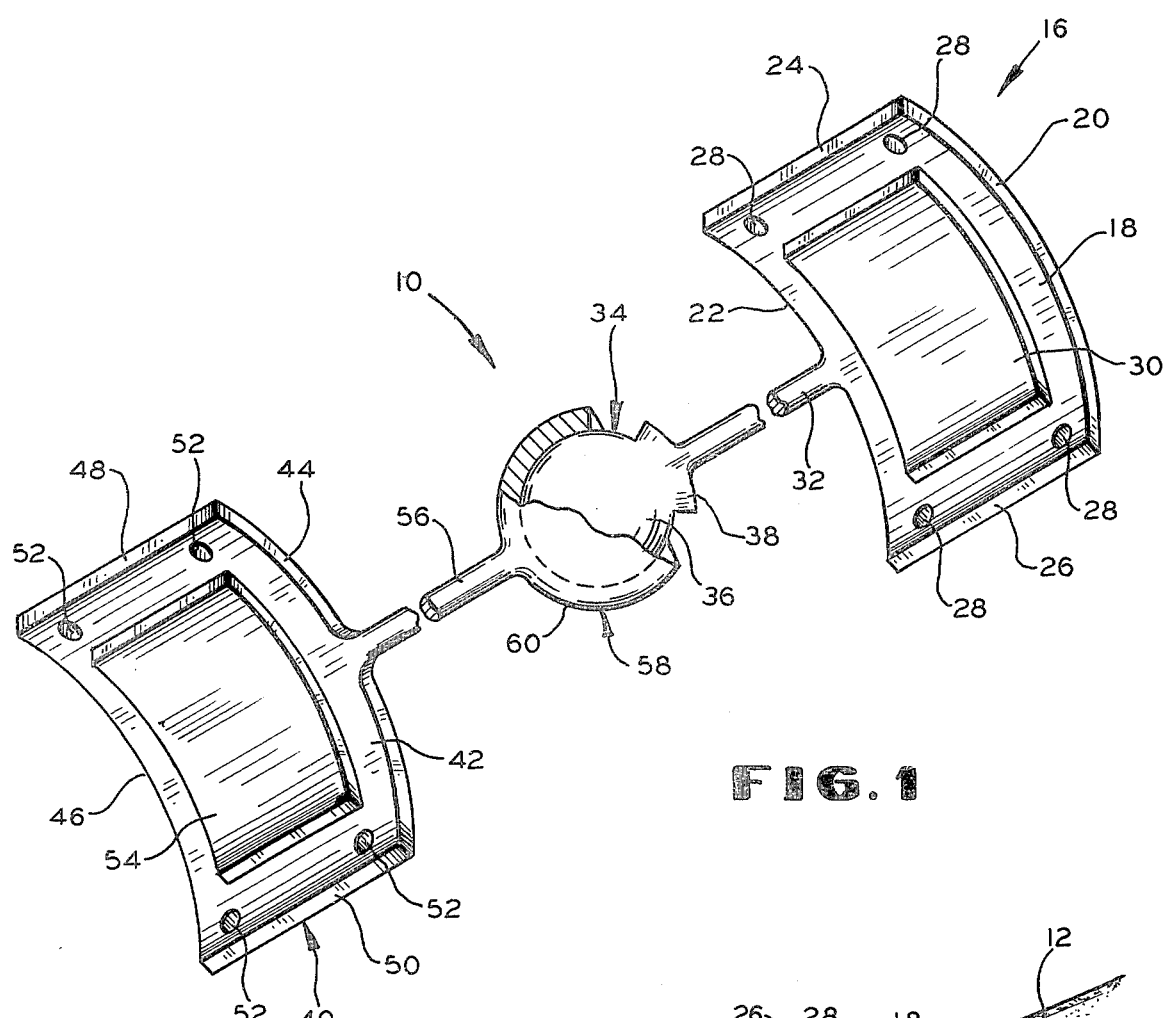
FIG. 1 is a fragmentary perspective view of an orthopedic apparatus for assisting in rotary motion and support of an affected bone joint, according to the present invention.
Figure 2:
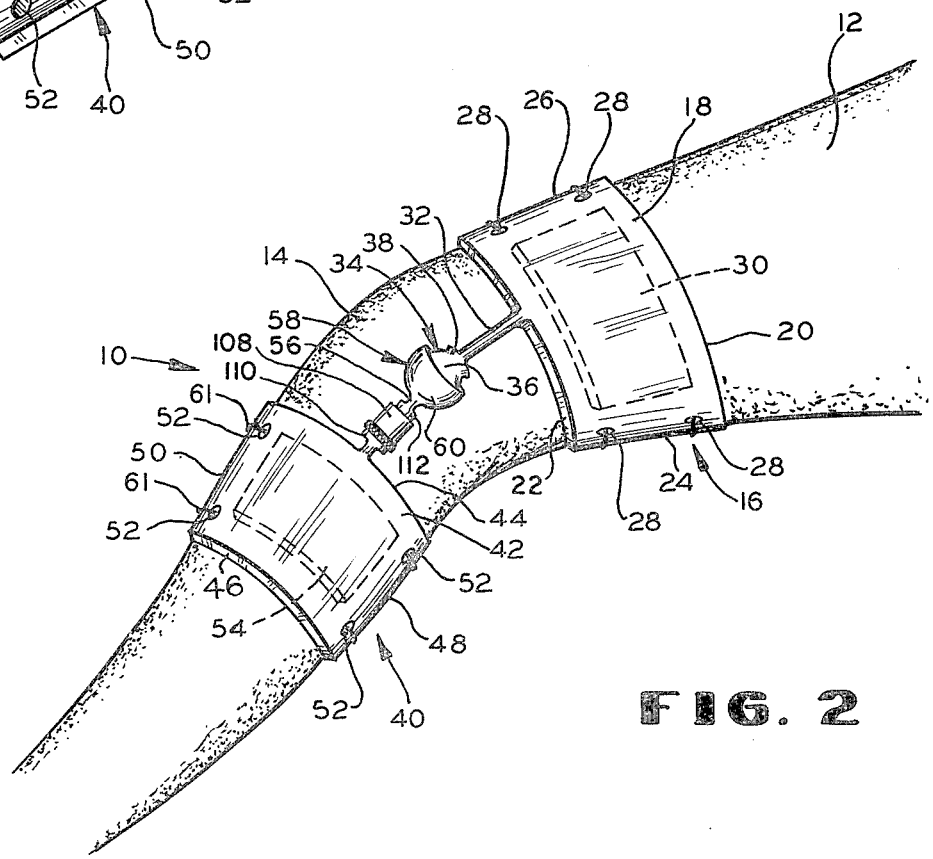
FIG. 2 is a perspective view of the invention illustrated in FIG. 1 attached to a human leg to support a knee joint.

There is shown in FIG. 1 an orthopedic apparatus 10 according to the present invention. There is shown in FIG. 2 the orthopedic apparatus 10 installed on a mammalian appendage, in particular, a human leg 12 such that the apparatus 10 provides support and protection for a knee joint 14. The orthopedic apparatus 10 includes a first support member 16, which is C-shaped in lateral section and is typically fabricated of steel or a chromium-vanadium alloy. The support member 16 is formed to be secured to a lateral aspect of the leg. The first support member 16 includes a main body portion 18 having an upper edge 20, a lower edge 22 and a pair of lateral edges 24 and 26. A plurality of apertures 28 are formed near the lateral edges 24 and 26 for securing the main body portion 18 of the first support member 16 to the appendage as will be discussed in detail hereinafter. A cushion member 30 is secured to the inner surface of the first support member 16 to cushion the engagement of the first support member 16 with the leg 12.

A first rigid arm 32 extends from the lower edge 22 of the main body 18 and terminates in a male member 34.

In the preferred embodiment, the male member 34 includes a spherically shaped ball 36 which has a shank 38 formed thereon.

The orthopedic apparatus 10 also includes a second support member 40 having a main body portion 42 including an upper edge 44, a lower edge 46, and a pair of lateral edges 48 and 50. A plurality of apertures 52 are formed near the lateral edges 48 and 50. A cushion member 54 is secured to the concave surface of the main body portion 42 to cushion the attachment of the second support member 40 to the leg 12.

A second rigid arm 56 extends from the upper edge 44 of the main body 42. The second rigid arm 56 terminates in a female member 58 including a generally cup shaped socket 60. The socket 60 is complimentary in geometry to the ball 36 of the male member 34 such that when the male member 34 is inserted into the female member 58, there is formed a ball and socket joint.

As shown in FIG. 2, the orthopedic apparatus 10 is utilized by inserting the male member 34 into the female member 58 to form a ball and socket joint and then securing the assembled apparatus 10 to one lateral aspect of the leg 12. The apparatus 10 can be used alone as shown in FIG. 2, or used in connection with a second complementary apparatus, which can be placed on the opposite medial aspect of the leg 12. Rawhide straps 61 (shown in FIG. 2) can be threaded through the apertures 28 and 52 and tied around the leg 12 to secure the apparatus 10 to the lateral aspect of the leg 12.

As shown in FIG. 2, when secured to the leg 12, the apparatus 10 provides a ball and socket joint adjacent to the ball and socket joint of the affected bone joint. When the bone joint is flexed to bring the distal portion of the leg to the rear of the patient, the knee joint 14 flexes in its natural fashion and the ball and socket joint of the apparatus 10 flexes in the same fashion. Note that the ball and socket joint allows support of the patient's knee joint 14 not only for motion in a single plane, the typical forward and backward motion of the knee joint, but also assists in the rotary motion of the knee joint. The shank 38 is formed on the upper portion of the male member 34 so that the ball and socket joint is free to track the movement of the patient's knee joint 14 in its normal path of travel, but will not allow extreme flex in either the lateral aspects or the anterior aspect of its flexation. Therefore, the shank 38 serves to partially limit the flex of the knee joint 14 when such limitation on its rotary motion is in the best therapeutic interest of the patient. The posterior portion of the shank 38 is eliminated from the male member 34 to allow normal flex of the knee joint 14.

In some clinical applications, it may be advisable to secure the apparatus 10 directly to the affected appendage without the benefit of an intervening garmet. In this case, to prevent any discomfort associated with placing cold metal against the leg the entire apparatus, with the exception of the male and female members, can be coated with a suitable coating. For example, a plastic laminate film or a leather sleeve can be used, which will insulate the leg from the cold metal underlying the laminate or sleeve.

Figure 3:
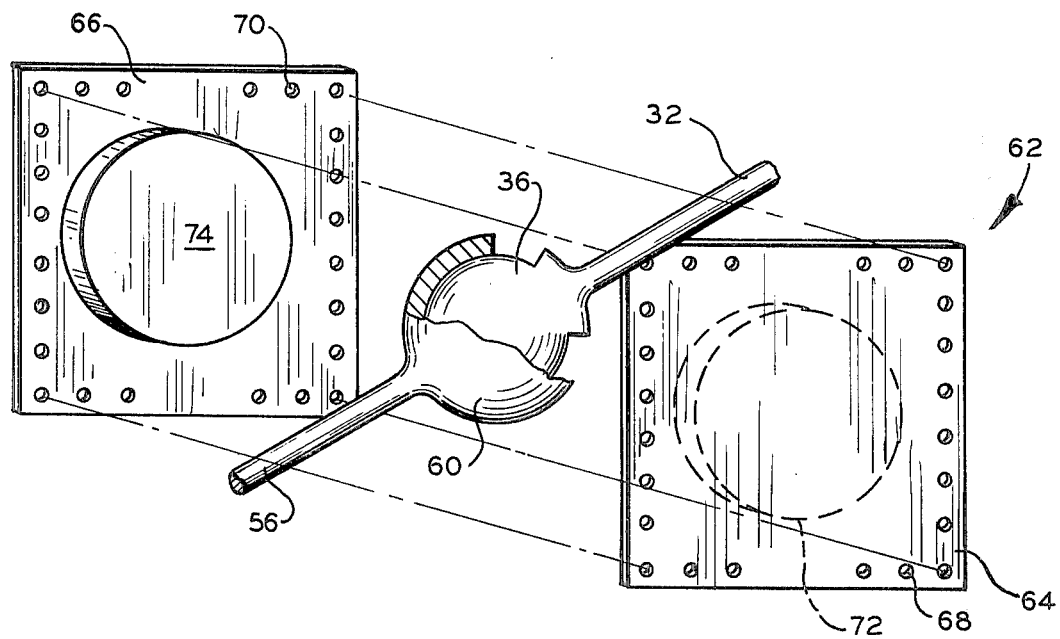
FIG. 3 is an exploded view of a protective closure capable of surrounding the male and female members of the invention illustrated in FIG. 1.

In the preferred embodiment, as shown in FIG. 3, the ball and socket joint itself is spaced apart from the outer surface of the leg 12 adjacent the knee joint 14 by a protective closure 62. The protective closure 62 includes a pair of closure walls 64 and 66. A plurality of apertures 68 and 70 are formed about the periphery of the closure walls 64 and 66 respectively. Closure wall pads 72 and 74 are formed on the interior surface of the closure walls 64 and 66 respectively to cushion the contact of the ball and socket joints against the outer surface of the leg 12. The closure walls 64 and 66 are placed around the ball and socket joint and laced together by rawhide straps (not shown) or other suitable closure means to form a protective closure which surrounds the ball and socket joint and cushions the contact of the ball and socket joint with the leg 12.

In the preferred embodiment of the orthopedic apparatus 10 shown in FIGS. 1 and 2, the first and second support members 16 and 40 are secured to the lateral aspect of the leg 12 by lacing rawhide straps 61 through the apertures 28 and 52 in the first and second support members 16 and 40 respectively, and tying the straps 61 together on the opposite medial aspect of the leg. In the event two apparatuses 10 are needed, one apparatus is placed on each aspect of the leg 12, and the two apparatuses are linked together by lacing rawhide straps 61 through the apertures in the apparatuses and tying the straps 61 to secure the apparatuses to the affected leg 12.

Figure 4A:
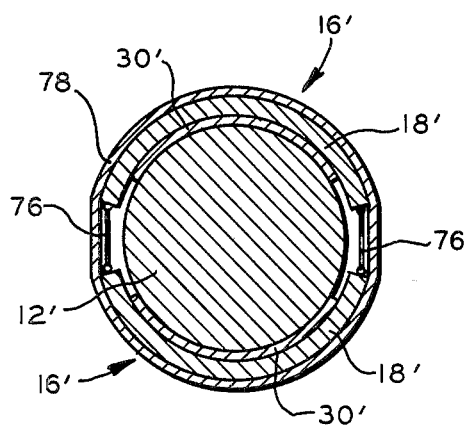
FIGS. 4a through 4c are cross-sectional views of various embodiments of means for securing the support members to an affected appendage.
Figure 4B:
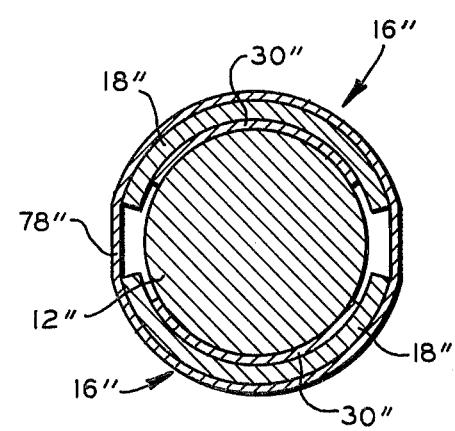
Figure 4C:
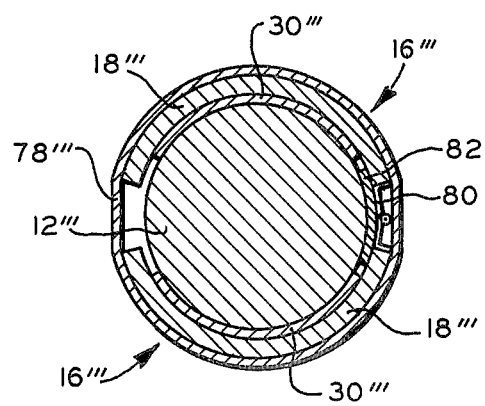

FIGS. 4a through 4c show some alternative methods which can be used to secure the support members to the leg 12. FIG. 4a is a cross-sectional view taken through the main body portions 18' of a pair of first support members 16' in contact with a leg 12' above the knee joint. Rawhide straps 76 are used to tie the support members together. Generally, after the support member 16' has been securely tied in intimate contact with the leg 12, an elastic bandage 78 is placed around the support member 16' to assist in maintaining the support member 16' in intimate contact with the leg. The same procedure is used to secure a pair of second support members (not shown) to the leg 12. FIG. 4b shows an alternative embodiment wherein only an elastic bandage 78' is used to secure the first support members 16" to the leg 12". Alternatively, as shown in FIG. 4c, the first support members 16''' can be joined together by a spring hinge 80 at the posterior of the leg, provided that, the spring hinge is separated from the leg 12''' by a protective liner 82. The spring hinge can include a pair of springs, if advantageous. As in the other embodiments, the elastic bandage 78''' can be employed to assist in securing the support members in intimate contact with the leg 12'''.

During normal service, no active mechanical support is needed to maintain the ball 36 in the socket 60. The opening in the socket is slightly smaller in diameter than the ball. The ball and socket are assembled by heating the socket 60 to a fairly high temperature and lowering the temperature of the ball 36 so that the socket expands and the ball contracts to allow the ball 36 to pass through the hole in the socket 60. After the ball 36 has been placed in the socket 60, the ball 36 and socket 60 are allowed to come to room temperature to assume their normal geometries. This operation secures the ball 36 within the socket 60 while allowing it free rotary movement within the path of travel defined by the shank 38.

Figure 5:
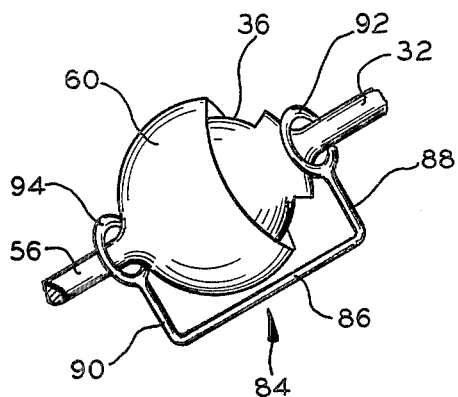
FIG. 5 is a perspective view of a restraining collar according to the present invention.

In some instances, however, the ball 36 and socket 60 are stressed to the point where they could disengage from one another. FIG. 5 shows an embodiment of the invention wherein a restraining collar 84 is used to maintain the ball 36 and socket 60 in contact with each other during periods of excess stress which would cause them to disengage. The restraining collar 84 includes a back plate 86 with outwardly depending legs 88 and 90. The leg 88 terminates in a metal ring 92, while the leg 90 terminates in a metal ring 94. The rings 92 and 94 surround the first rigid arm 32 and second rigid arm 56 respectively. The rings 92 and 94 are positioned near enough to the ball 36 and the cup 60 to restrain their motion along the longitudinal axis defined by the first and second rigid arms 32 and 56. Thus, the restraining collar 84 serves to hold the ball 36 within the socket 60 when there is sufficient stress to cause the ball 36 to disengage from the socket 60.

Figure 6:
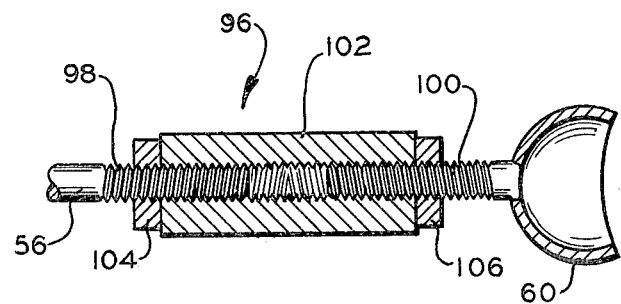
FIG. 6 is a cross-sectional view of a tension adjusting device according to the present invention.

In some cases it is advisable to increase the tension between the first support member 16 and the second support member 40 as much as possible without causing the ball 36 to disengage with socket 60 in flexion. In this case, a tension adjusting device 96, shown in FIG. 6 as a turn buckle, is employed to provide the necessary tension between the support members 16 and 40. The tension adjusting device 96 can be placed in either the rigid arm 32 or 56. In FIG. 6, the rigid arm 56 is separated and external threads 98 and 100 are formed on the facing ends. The threads 98 are typically left-hand threads while the threads 100 are typically right-hand threads. An internally threaded housing 102 is formed to accept the threaded ends of the arm 56. As the internally threaded housing 102 is rotated, the two portions of the arm 56 are threadingly engaged and drawn outwardly of the housing 102. When sufficient tension has been achieved between the support members 16 and 40, rotation of the housing 102 is stopped. To maintain the appropriate tension, a pair of internally threaded locking nuts 104 and 106 are rotated until they engage the ends of the housing 102. The locking nuts hold the two parts of the arm 56 within the housing 102 to maintain the desired tension between the support members 16 and 40.

Figure 7:
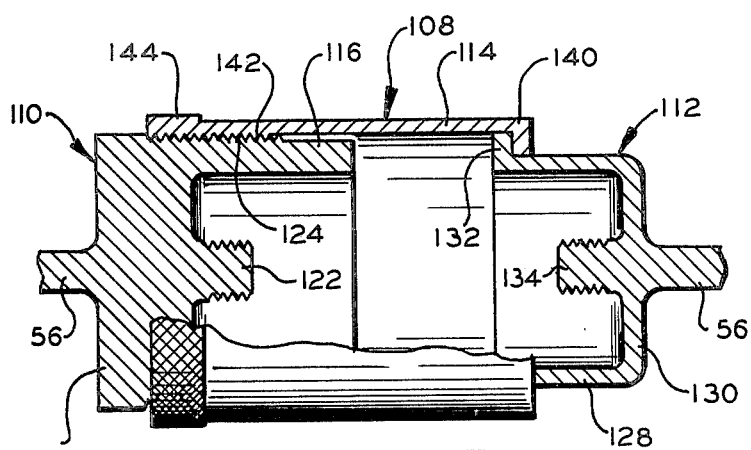
FIG. 7 is a fragmentary cross-sectional view of a shock absorber receiver.

In some cases, it is advisable to include a shock absorbing device in one of the rigid arms to absorb extreme vertical stresses which could be placed upon the ball and socket joint from impacts which could be experienced by wearers, for example, athletes. FIG. 7 shows a fragmentary cross-sectional view of a shock absorber receiver 108 capable of accepting a shock absorbing insert, described in detail hereinafter. For purposes of illustration, the receiver 108 is shown integral with the second rigid arm 56 of the apparatus 10. The receiver 108 includes a first housing 110, a second housing 112 and a restraining sleeve 114. The first housing 110 is generally cup shaped with a closed end formed integral with the rigid arm 56 of the apparatus 10. The first housing includes wall 116 which terminates in a closed end 120. A threaded stud 122 is formed in the center of the end inside the housing 120. A set of threads 124 are formed on the outer surface of the wall 116. The second housing 112 is also cup shaped with a wall 128 and a closed end 130. The wall 128 terminates opposite the closed end in a flange 132. The closed end 130 includes a centrally located threaded stud 134, formed inside the housing.

The first housing 110 and the second housing 112 are held together by the restraining sleeve 114. The restraining sleeve 114 has a flange 140 formed at one end and an internal set of threads 142, which are adapted to engage the threads 124 on the first housing 110, formed at the other end. A knurled area 144 is included on the exterior surface of the sleeve 114 to assist in snugly securing the first housing 110 to the sleeve 114.

Figure 8:
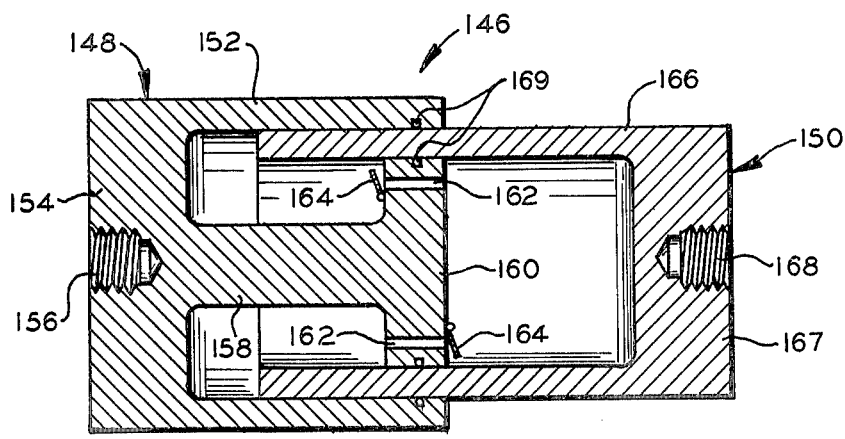
FIG. 8 is a cross-sectional view of a shock absorbing device.

FIG. 8 shows one embodiment of a shock absorbing device 146 which can be utilized with the receiver 108. The device includes a piston housing 148 and a cylinder housing 150. The piston housing 148 is generally cup shaped and includes a wall 152 and an enclosed end 154. The end 154 has a threaded aperture 156 formed thereon for engaging the threaded stud 122 of the receiver 108. The end 154 also has a central post 158 formed therein which extends into the cup shaped cavity defined by the wall 152. A piston 160 is attached to the end of the post 158 and has a pair of apertures 162 formed therein connecting the opposite faces of the piston 160. A flap valve 164 is attached to each of the opposing surfaces of the piston to cover one end of each of the apertures 162.

The cylinder housing 150 is generally cup shaped and includes a wall 166 and an enclosed end 167. The end 167 has a threaded aperture 168 formed therein for engaging the threaded stud 134 of the receiver 108. The piston 160 is sealed to the internal surface of the wall 166 and the external surface of the wall 166 is sealed to the internal surface of the wall 152 by a pair of O-rings 169. The cavities formed on either side of the piston 160 can be filled with hydraulic fluid through access holes (not shown). The flap valves 164 allow the passage of the hydraulic fluid in one direction, one operating during compression and one during decompression.

Figure 9:
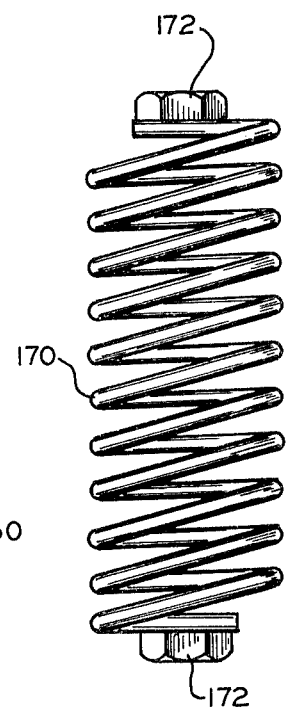
FIG. 9 is an elevational view of an alternative embodiment of a shock absorbing device.

FIG. 9 shows an alternative embodiment of a shock absorbing device for use with the receiver 108. A helical spring 170 has a pair of internally threaded nuts 172 attached to the opposite ends thereof. The nuts are threadably engaged by the studs 122 and 134 in the receiver 108.

In summary, the present invention concerns an orthopedic apparatus capable of supporting and protecting a bone joint while allowing rotary movement and flexion of the joint when the apparatus is in place. The apparatus includes a first support member which is secured to an affected appendage on one side of the joint to be treated. A first rigid arm extends from the first support member and terminates in a ball adjacent the joint. The ball seats into a socket which is attached to a second rigid arm which extends from a second support member. The first and second support members are brought into intimate contact with the appendage and secured thereto by an elastic bandage and/or with rawhide straps threaded through apertures in the support members.

In accordance with the provisions of the patent statutes, the principle and mode of operation of the invention have been explained and illustrated in its preferred alternative embodiments. However, it must be understood that the invention may be practiced otherwise then as specifically illustrated and described without departing from its spirit or scope.

What is claimed is:

1. An orthopedic apparatus for supplementing bone joint functions in an appendage comprising:
   a first support member having a cushion member attached thereto for contacting an appendage;
   means for securing said first support member to an appendage on one side of a bone joint;
   a first rigid arm extending from said first support member and terminating in a ball member of the ball and socket joint positioned such that when said first support is secured to an appendage on one side of a bone joint the ball member of the ball and socket joint is located adjacent a bone joint;
   a second support member having a cushion member attached thereto for contacting an appendage;

means for securing said second support member to an appendage on the other side of a bone joint;

a second rigid arm extending from said second support member and terminating in a socket member of a ball and socket joint positioned such that when said first support is secured to an appendage on the other side of the bone joint the socket member of the ball and socket joint is located adjacent the bone joint, said ball and socket joint including a sperically shaped ball retained by a generally cup-shaped socket, said socket being mounted on said second arm such that the socket axis, defined by the line through the center of the opening of said socket and the center of the bottom portion of said socket, is aligned with the axis of said second arm; and one of said rigid arms having shock absorbing means connected intermediate its opposite ends.

2. An apparatus according to claim 1 wherein said first and second support members have apertures formed therein and said means for securing said first and second support members includes rawhide straps which are laced through said apertures and tied around an appendage.

3. An apparatus according to claim 2 wherein said means for securing said first and second support members includes elastic bandages placed around said support members and an appendage.

4. An apparatus according to claim 1 wherein said ball has a shank formed thereon for limiting flexion of a bone joint.

5. An apparatus according to claim 1 wherein said shock absorbing means includes a receiver formed integral with and intermediate opposite ends of said one rigid arm, said receiver including first and second housings forming an enclosure for a shock absorbing device, and a shock absorbing device.

6. An apparatus according to claim 5 wherein said shock absorbing device is a hydraulic shock absorber.

7. An apparatus according to claim 5 wherein said shock absorbing device is a helical spring.

8. An apparatus according to claim 1 wherein one of said first and second rigid arms includes tension adjusting means.

9. An apparatus according to claim 1 including a second orthopedic apparatus wherein said first support members are connected together and said second support members are connected together at an posterior of the appendage by spring hinges.

10. An orthopedic apparatus for supplementing bone joint functions in an appendage comprising:

a first support member having a cushion member attached thereto for contacting an appendage;
means for securing said first support member to an appendage on one side of a bone joint;
a first rigid arm extending from said first support member and terminating in a ball positioned such that when said first support is secured to an appendage on one side of a bone joint said ball is located adjacent the bone joint;
a second support member having a cushion member attached thereto for contacting an appendage;
means for securing said second support member to an appendage on the other side of a bone joint;
a second rigid arm extending from said second support member and terminating in a generally cup shaped socket positioned such that when said second support is secured to an appendage on the other side of the bone joint said socket is located adjacent the bone joint, said ball and said socket cooperating as a ball and socket joint, said ball being sperically shaped and retained by said generally cup shaped socket, said socket being mounted on said second arm such that the socket axis, defined by the line through the center of the opening of said socket and the center of the bottom portion of said socket, is aligned with the axis of said second arm; and
one of said rigid arms having shock absorbing means connected intermediate its opposite ends.

11. An apparatus according to claim 10 wherein said ball has a shank formed thereon for limiting flexion of a bone joint.

12. An apparatus according to claim 10 wherein said shock absorbing means includes a receiver attached intermediate the ends of said one rigid arm and a shock absorbing device enclosed by said receiver.

13. An orthopedic apparatus for supplementing bone joint functions in an appendage comprising:

a first support member having a cushion attached thereto for contacting an appendage;
means for securing said first support member to an appendage on one side of a bone joint;
a first rigid arm extending from said first support member and terminating in a ball member of a ball and socket joint adjacent a bone joint;
a second support member having a cushion member attached thereto for contacting an appendage;
means for securing said second support member to an appendage on the other side of the bone joint;
a second rigid arm extending from said second support member and terminating in a socket member of a ball and socket joint; and
wherein said ball and socket joint members include a sperically shaped ball retained by a generally cup shaped socket, and a shank formed on said ball for cooperating with said socket to limit flexion of a bone joint, said shank being located at the point of attachment of the first arm to the ball member and being wider than the width of the first arm at the point of attachment.

* * * * *